US010323069B2

(12) United States Patent
Murtaugh et al.

(10) Patent No.: US 10,323,069 B2
(45) Date of Patent: Jun. 18, 2019

(54) *SENECAVIRUS A* ANTIGENS AND METHODS OF USE (71) Applicant: REGENTS OF THE UNIVERSITY OF MINNESOTA, Minneapolis, MN (US)

(72) Inventors: Michael Murtaugh, St. Paul, MN (US); Cheryl Dvorak, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/684,358

(22) Filed: Aug. 23, 2017

(65) Prior Publication Data

US 2018/0057541 A1    Mar. 1, 2018

Related U.S. Application Data

(60) Provisional application No. 62/378,324, filed on Aug. 23, 2016.

(51) Int. Cl.
| | |
|---|---|
| *C07K 14/005* | (2006.01) |
| *C07K 17/00* | (2006.01) |
| *C07K 16/10* | (2006.01) |
| *A61K 39/125* | (2006.01) |
| *C12N 7/00* | (2006.01) |
| *G01N 33/569* | (2006.01) |
| *A61K 39/12* | (2006.01) |
| *A61K 39/00* | (2006.01) |

(52) U.S. Cl.
CPC ............ *C07K 14/005* (2013.01); *A61K 39/12* (2013.01); *A61K 39/125* (2013.01); *C07K 16/1009* (2013.01); *C07K 17/00* (2013.01); *C12N 7/00* (2013.01); *G01N 33/56983* (2013.01); *A61K 2039/575* (2013.01); *C12N 2770/32021* (2013.01); *C12N 2770/32022* (2013.01); *C12N 2770/32034* (2013.01); *G01N 2333/085* (2013.01); *G01N 2469/20* (2013.01)

(58) Field of Classification Search
None
See application file for complete search history.

(56) References Cited

U.S. PATENT DOCUMENTS

2018/0057541 A1* 3/2018 Murtaugh .............. A61K 39/12

FOREIGN PATENT DOCUMENTS

WO    WO 2005/030139    * 4/2005

OTHER PUBLICATIONS

Sequence alignment of 147-284 of SEQ ID No. 1 with Geneseq access No. ADZ15013 by Hallenbeck et al 2005.*
Sequence alignment of 435-673 of SEQ ID No. 1 with Geneseq access No. ADZ15047 by Hallenbeck et al 2005.*
Zhang et al. (Frontiers in Microbiology. May 2018; 9 (Article 940); doi: 103389/fmicb.2018.0940).*
Adams, "Ratification vote on taxonomic proposals to the International Committee on Taxonomy of Viruses" Jul. 2015 *Arch Virol.*, 160(7):1837-1850.
Bracht, "Real-Time Reverse Transcription PCR Assay for Detection of Senecavirus A in Swine Vesicular Diagnostic Specimens" 2016 *PLoS One*, 11(1):e0146211.
Dvorak, "National reduction in porcine circovirus type 2 prevalence following introduction of vaccination" 2016 *Veterinary Microbiology*, 189:86-90.
GenBank "AGM16001.1" Online: https://www.ncbi.nlm.nih.gov/protein/AGM16001.1.
Hales, "Complete genome sequence analysis of Seneca Valley virus-001, a novel oncolytic picornavirus" May 2008 *J Gen Virol.*, 89(Pt 5):1265-1275.
Leme, "Senecavirus A: An Emerging Vesicular Infection in Brazilian Pig Herds" 2015 *Transbound Emerg Dis.*, 62(6):603-611.
Pasma, "Idiopathic vesicular disease in swine in Manitoba" Jan. 2008 *Can Vet J*, 49(1):84-85.
Puvanendiran, "Absence of porcine circovirus type 1 (PCV1) and high prevalence of PCV 2 exposure and infection in swine finisher herds" 2011 *Virus Res.*, 157(1):92-98.
Rudin, "Phase I clinical study of Seneca Valley Virus (SVV-001), a replication-competent picornavirus, in advanced solid tumors with neuroendocrine features" Feb. 2011 *Clin Cancer Res.*, 17(4):888-895.
United States Animal Health Association (USAHA), "Resolution 2012. Research on Seneca Valley Virus" In paper presented at 116th Annual Meeting. Greensboro, NC; Oct. 2012, 2 pages.
Vannucci, "Identification and Complete Genome of Seneca Valley Virus in Vesicular Fluid and Sera of Pigs Affected with Idiopathic Vesicular Disease, Brazil" 2015 *Transbound Emerg Dis.*, 62(6):589-593.
Yang, "Generation and diagnostic application of monoclonal antibodies against Seneca Valley virus" Jan. 2012 *J Vet Diagn Invest.*, 24(1):42-50.

* cited by examiner

*Primary Examiner* — Shanon A. Foley
(74) *Attorney, Agent, or Firm* — Mueting, Raasch & Gebhardt, PA (57) ABSTRACT

A *Senecavirus* A polypeptide generally includes at least a portion of 151-434 of SEQ ID NO:1, amino acids 435-673 of SEQ ID NO:1, or amino acids 674-937 of SEQ ID NO:1. The *Senecavirus* A polypeptide may be used as a capture antigen in a method or device for detecting antibody that specifically binds to the *Senecavirus* A polypeptide. The *Senecavirus* A polypeptide may be used as a immunogen to vaccinate a subject having or at risk of having a *Senecavirus* A infection.

7 Claims, 4 Drawing Sheets
Specification includes a Sequence Listing.

SEQUENCE LISTING

<160> NUMBER OF SEQ ID NOS: 3

<210> SEQ ID NO 1
<211> LENGTH: 2181
<212> TYPE: PRT
<213> ORGANISM: Senecavirus A

<400> SEQUENCE: 1

Met Gln Asn Ser His Phe Ser Phe Asp Thr Ala Ser Gly Thr Phe Glu
1               5                   10                  15

Asp Val Thr Gly Thr Lys Val Lys Ile Val Glu Tyr Pro Arg Ser Val
            20                  25                  30

Asn Asn Gly Val Tyr Asp Ser Ser Thr His Leu Glu Ile Leu Asn Leu
        35                  40                  45

Gln Gly Glu Ile Glu Ile Leu Arg Ser Phe Asn Glu Tyr Gln Ile Arg
    50                  55                  60

Ala Ala Lys Gln Gln Leu Gly Leu Asp Ile Val Tyr Glu Leu Gln Gly
65                  70                  75                  80

Asn Val Gln Thr Thr Ser Lys Asn Asp Phe Asp Ser Arg Gly Asn Asn
                85                  90                  95

Gly Asn Met Thr Phe Asn Tyr Tyr Ala Asn Thr Tyr Gln Asn Ser Val
            100                 105                 110

Asp Phe Ser Thr Ser Ser Ser Ala Ser Gly Ala Gly Pro Gly Asn Ser

```
            115                 120                 125
Arg Gly Gly Leu Ala Gly Leu Leu Thr Asn Phe Ser Gly Ile Leu Asn
    130                 135                 140

Pro Leu Gly Tyr Leu Lys Asp His Asn Thr Glu Glu Met Glu Asn Ser
145                 150                 155                 160

Ala Asp Arg Val Ile Thr Gln Thr Ala Gly Asn Thr Ala Ile Asn Thr
                165                 170                 175

Gln Ser Ser Leu Gly Val Leu Cys Ala Tyr Val Glu Asp Pro Thr Lys
            180                 185                 190

Ser Asp Pro Pro Ser Ser Thr Asp Gln Pro Thr Thr Phe Thr
        195                 200                 205

Ala Ile Asp Arg Trp Tyr Thr Gly Arg Leu Asn Ser Trp Thr Lys Ala
    210                 215                 220

Val Lys Thr Phe Ser Phe Gln Ala Val Pro Leu Pro Gly Ala Phe Leu
225                 230                 235                 240

Ser Arg Gln Gly Gly Leu Asn Gly Gly Ala Phe Thr Ala Thr Leu His
                245                 250                 255

Arg His Phe Leu Met Lys Cys Gly Trp Gln Val Gln Val Gln Cys Asn
            260                 265                 270

Leu Thr Gln Phe His Gln Gly Ala Leu Leu Val Ala Met Val Pro Glu
        275                 280                 285

Thr Thr Leu Asp Val Lys Pro Asp Gly Lys Ala Lys Ser Leu Gln Glu
    290                 295                 300

Leu Asn Glu Glu Gln Trp Val Glu Met Ser Asp Asp Tyr Arg Thr Gly
305                 310                 315                 320

Lys Asn Met Pro Phe Gln Ser Leu Gly Thr Tyr Tyr Arg Pro Pro Asn
                325                 330                 335

Trp Thr Trp Gly Pro Asn Phe Ile Asn Pro Tyr Gln Val Thr Val Phe
            340                 345                 350

Pro His Gln Ile Leu Asn Ala Arg Thr Ser Thr Ser Val Asp Ile Ser
        355                 360                 365

Val Pro Tyr Ile Gly Glu Thr Pro Thr Gln Ser Ser Glu Thr Gln Asn
    370                 375                 380

Ser Trp Thr Leu Leu Val Met Val Leu Val Pro Leu Asp Tyr Lys Glu
385                 390                 395                 400

Gly Ala Thr Thr Asp Pro Glu Ile Thr Phe Ser Val Arg Pro Thr Ser
                405                 410                 415

Pro Tyr Phe Asn Gly Leu Arg Asn Arg Tyr Thr Thr Gly Thr Asp Glu
            420                 425                 430

Glu Gln Gly Pro Ile Pro Thr Ala Pro Arg Glu Asn Ser Leu Met Phe
        435                 440                 445

Leu Ser Thr Ile Pro Asp Asp Thr Val Pro Ala Tyr Gly Asn Val Arg
    450                 455                 460

Thr Pro Pro Val Asn Tyr Leu Pro Gly Glu Ile Thr Asp Leu Leu Gln
465                 470                 475                 480

Leu Ala Arg Ile Pro Thr Leu Met Ala Phe Gly Arg Val Ser Glu Pro
                485                 490                 495

Glu Pro Ala Ser Asp Ala Tyr Val Pro Tyr Val Ala Val Pro Thr Gln
            500                 505                 510

Phe Asp Asp Lys Pro Leu Ile Ser Phe Pro Ile Thr Leu Ser Asp Pro
        515                 520                 525

Val Tyr Gln Asn Thr Leu Val Gly Ala Ile Ser Ser Asn Phe Ala Asn
    530                 535                 540
```

-continued

Tyr Arg Gly Cys Ile Gln Ile Thr Leu Thr Phe Cys Gly Pro Met Met
545                 550                 555                 560

Ala Arg Gly Lys Phe Leu Leu Ser Tyr Ser Pro Pro Asn Gly Thr Gln
            565                 570                 575

Pro Gln Thr Leu Ser Glu Ala Met Gln Cys Thr Tyr Ser Ile Trp Asp
            580                 585                 590

Ile Gly Leu Asn Ser Ser Trp Thr Phe Val Ile Pro Tyr Ile Ser Pro
            595                 600                 605

Ser Asp Tyr Arg Glu Thr Arg Ala Ile Thr Asn Ser Val Tyr Ser Ala
610                 615                 620

Asp Gly Trp Phe Ser Leu His Lys Leu Thr Lys Ile Thr Leu Pro Pro
625                 630                 635                 640

Asp Cys Pro Gln Lys Pro Cys Ile Leu Phe Phe Ala Ser Ala Gly Glu
            645                 650                 655

Asp Tyr Thr Leu Arg Leu Pro Val Asp Cys Asn Pro Ser Tyr Val Phe
            660                 665                 670

His Ser Thr Asp Asn Ala Glu Thr Gly Val Ile Glu Ala Gly Asn Thr
            675                 680                 685

Asp Thr Asp Phe Ser Gly Glu Leu Ala Ala Pro Gly Ser Asn His Thr
690                 695                 700

Asn Val Lys Phe Leu Phe Asp Arg Ser Arg Leu Leu Asn Val Ile Lys
705                 710                 715                 720

Val Leu Glu Lys Asp Ala Val Phe Pro Arg Pro Phe Pro Thr Glu Thr
            725                 730                 735

Gly Ala Gln Gln Asp Asp Gly Tyr Phe Cys Leu Leu Thr Pro Arg Pro
            740                 745                 750

Thr Val Ala Ser Arg Pro Ala Thr Arg Phe Gly Leu Tyr Val Asn Pro
            755                 760                 765

Ser Asp Ser Gly Val Leu Ala Asn Thr Ser Leu Asp Phe Asn Phe Tyr
770                 775                 780

Ser Leu Ala Cys Phe Thr Tyr Phe Arg Ser Asp Leu Glu Val Thr Val
785                 790                 795                 800

Val Ser Leu Glu Pro Asp Leu Glu Phe Ala Val Gly Trp Phe Pro Ser
            805                 810                 815

Gly Ser Glu Tyr Gln Ala Ser Ser Phe Val Tyr Asp Gln Leu His Val
            820                 825                 830

Pro Tyr His Phe Thr Gly Arg Thr Pro Arg Ala Phe Thr Ser Lys Gly
            835                 840                 845

Gly Lys Val Ser Phe Val Leu Pro Trp Asn Ser Val Ser Ser Val Leu
            850                 855                 860

Pro Val Arg Trp Gly Ala Ala Ser Lys Leu Ser Ser Ala Thr Arg Gly
865                 870                 875                 880

Leu Pro Ala His Ala Asp Trp Gly Thr Ile Tyr Ala Phe Val Pro Arg
            885                 890                 895

Pro Asn Glu Lys Lys Ser Thr Ala Val Lys His Val Ala Val Tyr Val
            900                 905                 910

Arg Tyr Lys Asn Ala Arg Ala Trp Cys Pro Ser Met Leu Pro Phe Arg
            915                 920                 925

Ser Tyr Lys Gln Lys Met Leu Met Gln Ser Gly Asp Ile Glu Thr Asn
            930                 935                 940

Pro Gly Pro Ala Ser Asp Asn Pro Ile Leu Glu Phe Leu Glu Ala Glu
945                 950                 955                 960

-continued

Asn Asp Leu Val Thr Leu Ala Ser Leu Trp Lys Met Val His Ser Val
            965                 970                 975

Gln Gln Thr Trp Arg Lys Tyr Val Lys Asn Asp Asn Phe Trp Pro Asn
            980                 985                 990

Leu Leu Ser Glu Leu Val Gly Glu Gly Ser Ile Ala Leu Ala Ala Thr
            995                 1000                1005

Leu Ser Asn Gln Ala Ser Val Lys Ala Leu Leu Gly Leu His Phe
    1010                1015                1020

Leu Ser Arg Gly Leu Asn Tyr Thr Asp Phe Tyr Ser Leu Leu Ile
    1025                1030                1035

Glu Lys Cys Ser Ser Phe Phe Thr Val Glu Pro Pro Pro Pro
    1040                1045                1050

Ala Glu Asn Leu Met Thr Lys Pro Ser Val Lys Ser Lys Phe Arg
    1055                1060                1065

Lys Leu Phe Lys Met Gln Gly Pro Met Asp Lys Val Lys Asp Trp
    1070                1075                1080

Asn Gln Ile Ala Ala Gly Leu Lys Asn Phe Gln Phe Val Arg Asp
    1085                1090                1095

Leu Val Lys Glu Val Val Asp Trp Leu Gln Ala Trp Ile Asn Lys
    1100                1105                1110

Glu Lys Ala Ser Pro Val Leu Gln Tyr Gln Leu Glu Met Lys Lys
    1115                1120                1125

Leu Gly Pro Val Ala Leu Ala His Asp Ala Phe Met Ala Gly Ser
    1130                1135                1140

Gly Pro Pro Leu Ser Asp Asp Gln Ile Glu Tyr Leu Gln Asn Leu
    1145                1150                1155

Lys Ser Leu Ala Leu Thr Leu Gly Lys Thr Asn Leu Ala Gln Ser
    1160                1165                1170

Leu Thr Thr Met Ile Asn Ala Lys Gln Ser Ser Ala Gln Arg Val
    1175                1180                1185

Glu Pro Val Val Val Leu Arg Gly Lys Pro Gly Cys Gly Lys
    1190                1195                1200

Ser Leu Ala Ser Thr Leu Ile Ala Gln Ala Val Ser Lys Arg Leu
    1205                1210                1215

Tyr Gly Ser Gln Ser Val Tyr Ser Leu Pro Pro Asp Pro Asp Phe
    1220                1225                1230

Phe Asp Gly Tyr Lys Gly Gln Phe Val Thr Leu Met Asp Asp Leu
    1235                1240                1245

Gly Gln Asn Pro Asp Gly Gln Asp Phe Ser Thr Phe Cys Gln Met
    1250                1255                1260

Val Ser Thr Ala Gln Phe Leu Pro Asn Met Ala Asp Leu Ala Glu
    1265                1270                1275

Lys Gly Arg Pro Phe Thr Ser Asn Leu Ile Ile Ala Thr Thr Asn
    1280                1285                1290

Leu Pro His Phe Ser Pro Val Thr Ile Ala Asp Pro Ser Ala Val
    1295                1300                1305

Ser Arg Arg Ile Asn Tyr Asp Leu Thr Leu Glu Val Ser Glu Ala
    1310                1315                1320

Tyr Lys Lys His Thr Arg Leu Asn Phe Asp Leu Ala Phe Arg Arg
    1325                1330                1335

Thr Asp Ala Pro Pro Ile Tyr Pro Phe Ala Ala His Val Pro Phe
    1340                1345                1350

Val Asp Val Ala Val Arg Phe Lys Asn Gly His Gln Asn Phe Asn

```
                1355                1360                1365
Leu Leu Glu Leu Val Asp Ser Ile Cys Ala Asp Ile Arg Ala Lys
                1370                1375                1380
Gln Gln Gly Ala Arg Asn Met Gln Thr Leu Val Leu Gln Ser Pro
                1385                1390                1395
Asn Glu Asn Asp Asp Thr Pro Val Asp Glu Ala Leu Gly Arg Val
                1400                1405                1410
Leu Thr Pro Ala Ala Val Asp Glu Ala Leu Val Asp Leu Ala Pro
                1415                1420                1425
Glu Ala Asp Pro Val Gly Arg Leu Ala Ile Leu Ala Lys Leu Gly
                1430                1435                1440
Leu Ala Leu Ala Ala Val Thr Pro Gly Leu Ile Ile Leu Ala Val
                1445                1450                1455
Gly Leu Tyr Arg Tyr Phe Ser Gly Ser Asp Thr Asp Gln Asp Glu
                1460                1465                1470
Thr Glu Cys Glu Glu Ser Thr Lys Ala Pro Arg Ser Glu Asn Ala
                1475                1480                1485
Tyr Asp Gly Pro Lys Lys Asn Ser Lys Pro Pro Gly Ala Leu Ser
                1490                1495                1500
Leu Met Glu Met Gln Gln Pro Asn Val Asp Met Gly Phe Glu Ala
                1505                1510                1515
Ala Val Ala Lys Lys Val Val Val Pro Ile Thr Phe Met Val Pro
                1520                1525                1530
Asn Arg Pro Ser Gly Leu Thr Gln Ser Ala Leu Leu Val Ala Gly
                1535                1540                1545
Arg Thr Phe Leu Ile Asn Glu His Thr Trp Ser Asn Pro Ser Trp
                1550                1555                1560
Thr Ser Phe Thr Ile Arg Gly Glu Val His Thr Arg Asp Glu Pro
                1565                1570                1575
Phe Gln Thr Val His Phe Thr His His Gly Val Pro Thr Asp Leu
                1580                1585                1590
Met Met Val Arg Leu Gly Pro Gly Asn Ser Phe Pro Asn Asn Leu
                1595                1600                1605
Asp Lys Phe Gly Leu Asp Gln Met Pro Ala Arg Asn Ser Arg Val
                1610                1615                1620
Val Gly Val Ser Ser Ser Tyr Gly Asn Phe Phe Ser Gly Asn
                1625                1630                1635
Phe Leu Gly Phe Val Asp Ser Ile Thr Ser Glu Gln Gly Thr Tyr
                1640                1645                1650
Ala Arg Leu Phe Arg Tyr Arg Val Thr Thr Tyr Lys Gly Trp Cys
                1655                1660                1665
Gly Ser Ala Leu Val Cys Glu Ala Gly Gly Val Arg Arg Ile Ile
                1670                1675                1680
Gly Leu His Ser Ala Gly Ala Ala Gly Ile Gly Ala Gly Thr Tyr
                1685                1690                1695
Ile Ser Lys Leu Gly Leu Ile Lys Ala Leu Lys His Leu Gly Glu
                1700                1705                1710
Pro Leu Ala Thr Met Gln Gly Leu Met Thr Glu Leu Glu Pro Gly
                1715                1720                1725
Ile Thr Val His Val Pro Arg Lys Ser Lys Leu Arg Lys Thr Thr
                1730                1735                1740
Ala His Ala Val Tyr Lys Pro Glu Phe Glu Pro Ala Val Leu Ser
                1745                1750                1755
```

```
Lys Phe Asp Pro Arg Leu Asn Lys Asp Val Asp Leu Asp Glu Val
    1760            1765            1770

Ile Trp Ser Lys His Thr Ala Asn Val Pro Tyr Gln Pro Pro Leu
    1775            1780            1785

Phe Tyr Thr Tyr Met Ser Glu Tyr Ala His Arg Val Phe Ser Phe
    1790            1795            1800

Leu Gly Lys Asp Asn Asp Ile Leu Thr Val Lys Glu Ala Ile Leu
    1805            1810            1815

Gly Ile Pro Gly Leu Asp Pro Met Asp Pro His Thr Ala Pro Gly
    1820            1825            1830

Leu Pro Tyr Ala Ile Asn Gly Leu Arg Arg Thr Asp Leu Val Asp
    1835            1840            1845

Phe Val Asn Gly Thr Val Asp Ala Ala Leu Ala Met Gln Ile Gln
    1850            1855            1860

Lys Phe Leu Asp Gly Asp Tyr Ser Asp His Val Phe Gln Thr Phe
    1865            1870            1875

Leu Lys Asp Glu Ile Arg Pro Ser Glu Lys Val Arg Ala Gly Lys
    1880            1885            1890

Thr Arg Ile Val Asp Val Pro Ser Leu Ala His Cys Ile Val Gly
    1895            1900            1905

Arg Met Leu Leu Gly Arg Phe Ala Ala Lys Phe Gln Ser His Pro
    1910            1915            1920

Gly Phe Leu Leu Gly Ser Ala Ile Gly Ser Asp Pro Asp Val Phe
    1925            1930            1935

Trp Thr Val Ile Gly Ala Gln Leu Glu Gly Arg Lys Asn Thr Tyr
    1940            1945            1950

Asp Val Asp Tyr Ser Ala Phe Asp Ser Ser His Gly Thr Gly Ser
    1955            1960            1965

Phe Glu Ala Leu Ile Ser Phe Phe Thr Val Asp Asn Gly Phe
    1970            1975            1980

Ser Pro Ala Leu Gly Pro Tyr Leu Arg Ser Leu Ala Val Ser Val
    1985            1990            1995

His Ala Tyr Gly Glu Arg Arg Ile Lys Ile Thr Gly Gly Leu Pro
    2000            2005            2010

Ser Gly Cys Ala Ala Thr Ser Leu Leu Asn Thr Val Leu Asn Asn
    2015            2020            2025

Val Ile Ile Arg Thr Ala Leu Ala Leu Thr Tyr Lys Glu Phe Glu
    2030            2035            2040

Tyr Asp Met Val Asp Ile Ile Ala Tyr Gly Asp Asp Leu Leu Val
    2045            2050            2055

Gly Thr Asp Tyr Asp Leu Asp Phe Asn Glu Val Ala Arg Arg Ala
    2060            2065            2070

Ala Lys Leu Gly Tyr Lys Met Thr Pro Ala Asn Lys Gly Ser Val
    2075            2080            2085

Phe Pro Pro Thr Ser Ser Leu Ser Asp Ala Val Phe Leu Lys Arg
    2090            2095            2100

Lys Phe Val Gln Asn Asn Asp Gly Leu Tyr Lys Pro Val Met Asp
    2105            2110            2115

Leu Lys Asn Leu Glu Ala Met Leu Ser Tyr Phe Lys Pro Gly Thr
    2120            2125            2130

Leu Leu Glu Lys Leu Gln Ser Val Ser Met Leu Ala Gln His Ser
    2135            2140            2145
```

-continued

```
Gly Lys Glu Glu Tyr Asp Arg Leu Met His Pro Phe Ala Asp Tyr
    2150            2155            2160

Gly Ala Val Pro Ser His Glu Tyr Leu Gln Ala Arg Trp Arg Ala
    2165            2170            2175

Leu Phe Asp
    2180

<210> SEQ ID NO 2
<211> LENGTH: 10
<212> TYPE: PRT
<213> ORGANISM: Artificial
<220> FEATURE:
<223> OTHER INFORMATION: polypeptide

<400> SEQUENCE: 2

Glu Gln Lys Leu Ile Ser Glu Glu Asp Leu
1               5                   10

<210> SEQ ID NO 3
<211> LENGTH: 6
<212> TYPE: PRT
<213> ORGANISM: Artificial
<220> FEATURE:
<223> OTHER INFORMATION: polypeptide

<400> SEQUENCE: 3

His His His His His His
1               5
```

SENECAVIRUS A ANTIGENS AND METHODS OF USE

CROSS-REFERENCE TO RELATED APPLICATION

This application claims priority to U.S. Provisional Patent Application No. 62/378,324, filed Aug. 23, 2016, which is incorporated herein by reference.

SEQUENCE LISTING

This application contains a Sequence Listing electronically submitted to the United States Patent and Trademark Office via EFS-Web as an ASCII text file entitled "11005540101SequenceListing_ST25.txt" having a size of 20 kilobytes and created on Aug. 22, 2017. Due to the electronic filing of the Sequence Listing, the electronically submitted Sequence Listing serves as both the paper copy required by 37 CFR § 1.821(c) and the CFR required by § 1.821(e). The information contained in the Sequence Listing is incorporated by reference herein.

SUMMARY

This disclosure describes, in one aspect, a device for detecting the presence of antibody that specifically binds to a *Senecavirus* A polypeptide in a sample. Generally, the device includes a substrate and a *Senecavirus* A polypeptide immobilized to the substrate. Generally, the *Senecavirus* A polypeptide includes at least a portion of amino acids 151-434 of SEQ ID NO:1, at least a portion of amino acids 435-673 of SEQ ID NO:1, or at least a portion of amino acids 674-937 of SEQ ID NO:1.

In some embodiments, the *Senecavirus* A polypeptide comprises at least a portion of amino acids 151-434 of SEQ ID NO:1.

In some embodiments, the *Senecavirus* A polypeptide comprises no more than 1000 amino acids of SEQ ID NO:1.

In some embodiments, the device can further include an antibody specifically bound to the *Senecavirus* A polypeptide.

In another aspect, this disclosure describes a method for detecting antibody that specifically binds to a *Senecavirus* A polypeptide in a biological sample obtained from a subject. Generally, the method includes contacting at least a portion of the sample with a *Senecavirus* A polypeptide, then detecting antibody from the biological sample specifically bound to the *Senecavirus* A polypeptide. Generally, the *Senecavirus* A polypeptide includes at least a portion of amino acids 151-434 of SEQ ID NO:1, at least a portion of amino acids 435-673 of SEQ ID NO:1, or at least a portion of amino acids 674-937 of SEQ ID NO:1.

In some embodiments, the *Senecavirus* A polypeptide is immobilized to a substrate.

In another aspect, this disclosure describes a composition that includes a *Senecavirus* A polypeptide and an adjuvant. Generally, *Senecavirus* A includes at least a portion of amino acids 151-434 of SEQ ID NO:1, at least a portion of amino acids 435-673 of SEQ ID NO:1, or at least a portion of amino acids 674-937 of SEQ ID NO:1.

In another aspect, this disclosure describes a method of treating a subject having or at risk of having a *Senecavirus* A infection. Generally, the method includes administering to the subject an amount of a composition effective to treat a *Senecavirus* A infection. The composition generally includes a *Senecavirus* A polypeptide and an adjuvant. Generally, the *Senecavirus* A polypeptide includes at least a portion of amino acids 151-434 of SEQ ID NO:1, at least a portion of amino acids 435-673 of SEQ ID NO:1, or at least a portion of amino acids 674-937 of SEQ ID NO:1.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. *Senecavirus* A (SVA) VP1, VP2, and VP3 purified proteins. SVA VP1, VP2, and VP3 genes were cloned and protein was expressed in *E. coli*. Expressed protein were eluted from cobalt affinity columns and visualized using SDS-PAGE. Left lane shows molecular weight markers (Bio-Rad laboratories, Inc., Hercules, Calif.). Samples are noted on the gel and approximate sizes for each protein are noted on the right side as approximated from the known size of the markers. The marker lane was from the same gel, but part of the image was removed for clarity.

FIG. 2. Time course of antibody responses to SVA VP1, VP2, and VP3. Serum samples collected from sows at the onset of clinical signs until 60 days later were tested in duplicate wells coated with 500 ng of each antigen. Negative control serum (Neg) was from a matched SVA-negative farm. Results are shown as a box whisker plot using the Tukey method for outliers for A) VP1, B) VP2, and C) VP3 proteins. The suspect positive OD range is shown as a grey bar with negatives below and positives above the bar.

FIG. 3. Avidity analysis on VP2 ELISA positive samples. An SVA VP2 avidity ELISA was performed and the avidity index (AI) calculated for each sample. The average AI over the time course is shown as a line using the right y-axis. The percent of samples with a low AI (<50%) at each time point is shown in light grey and the percent with a high AI (>50%) is shown in dark grey using the left y-axis.

FIG. 5. VP2 ELISA and IFA comparison. The percent of VP2 ELISA positive (closed circles) samples and the percent of IFA positive (open squares) and IFA suspect (closed squares) samples are shown over a 60-day time course.

DETAILED DESCRIPTION OF ILLUSTRATIVE EMBODIMENTS

Figure 1:
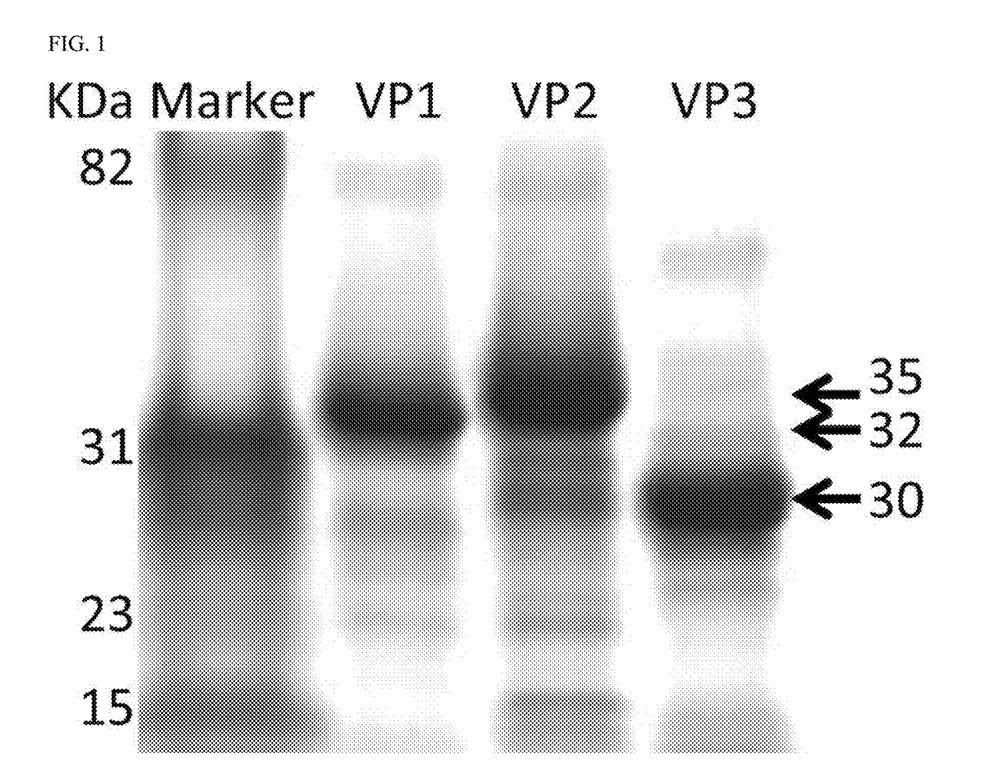
Figure 2:
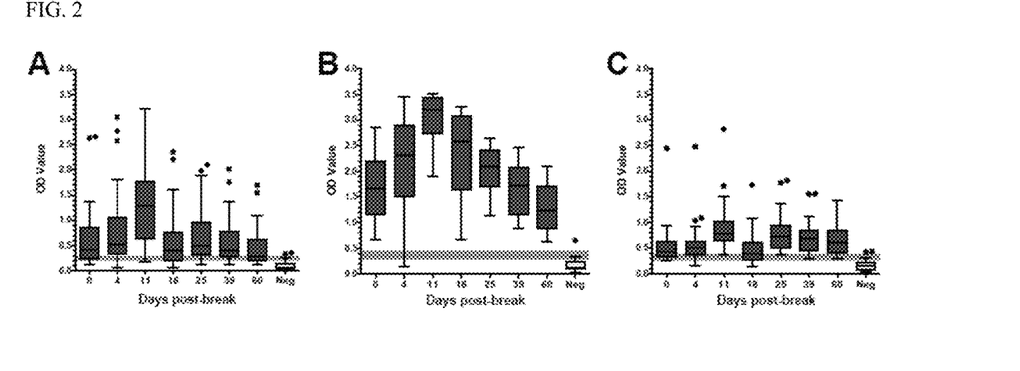
Figure 3:
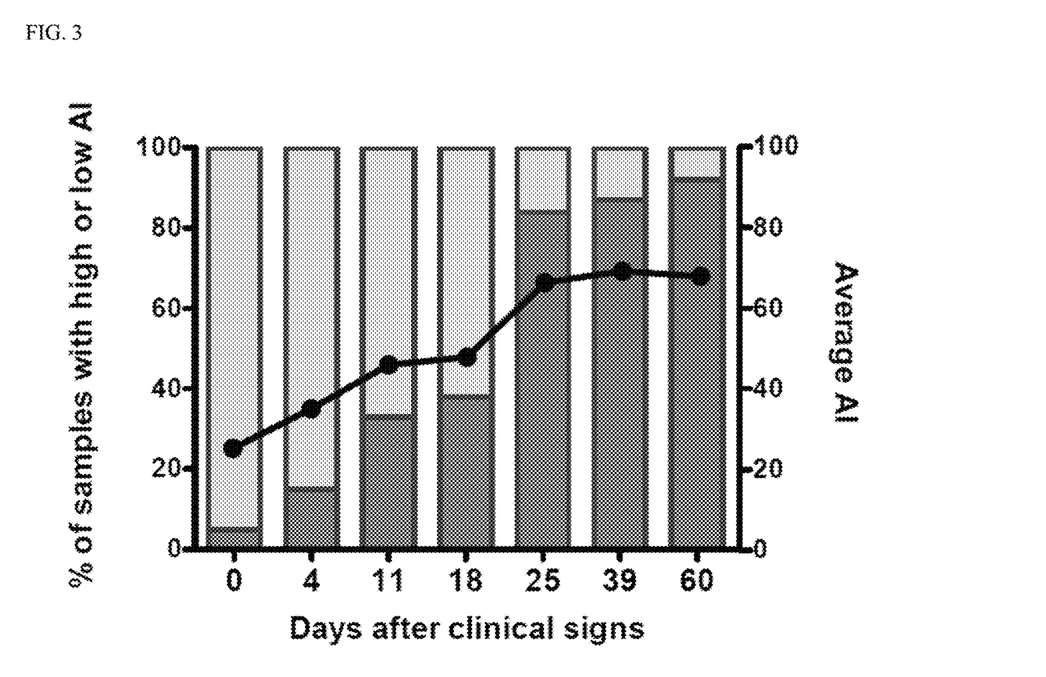
Figure 4:
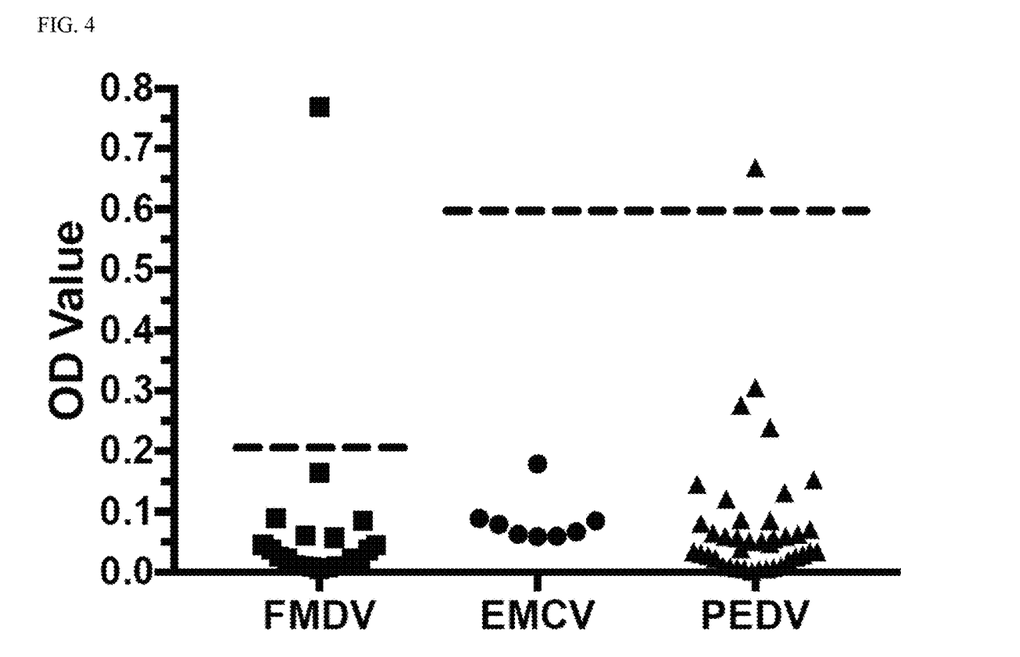
FIG. 4. Cross-reactivity analysis of SVA VP2 ELISA to other virus seropositive samples. SVA VP2 ELISA was performed on pig samples that were seropositive to other viruses (FMDV, EMCV, or PEDV), but whose SVA antibody status was unknown. The positive/negative cut-off values for EMCV and PEDV tested at the University of Minnesota, and FMDV tested at PIADC are shown by the dashed line.
Figure 5:
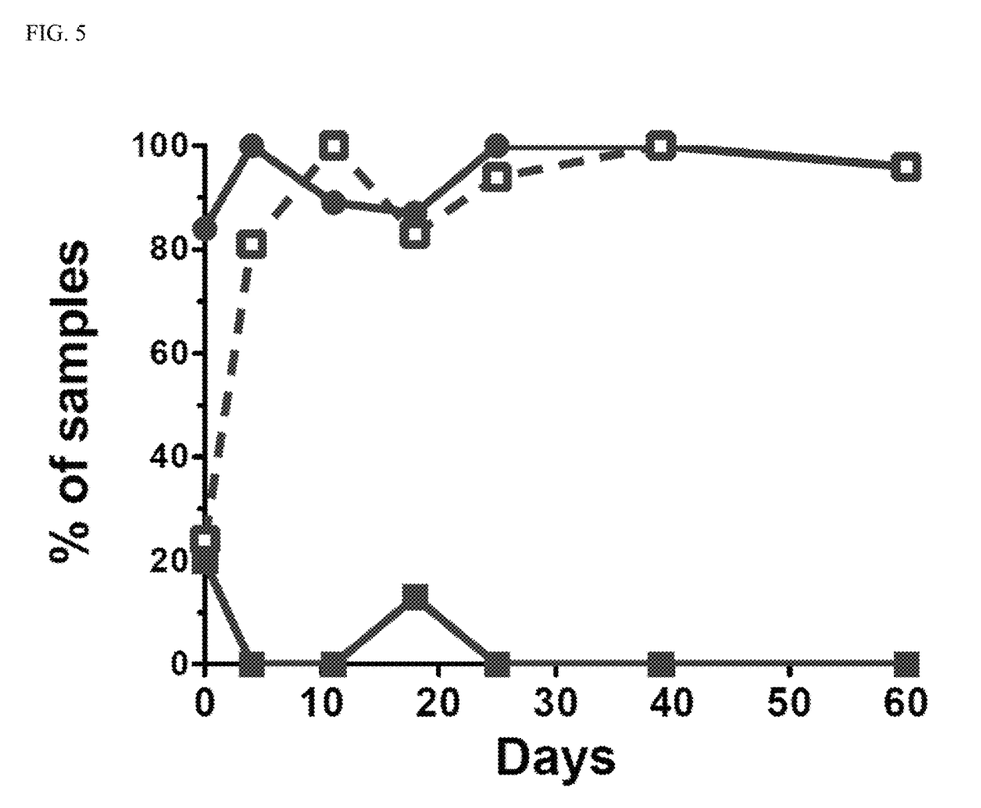

This disclosure describes an indirect ELISA assay to identify serum antibodies to the Seneca Valley virus *Senecavirus* A (SVA). Viral protein 1, 2, and 3 (VP1, VP2, VP3) were expressed, isolated, and purified from *E. coli* and used to coat plates for an indirect ELISA. Sera from pigs with and without idiopathic vesicular disease (IVD) symptoms were analyzed using this indirect ELISA to determine the antibody responses to VP1, VP2, and VP3. A time course study following animals from an infected farm was also performed using the ELISA. Antibody responses to VP2 were higher than VP1 and VP3 and showed high affinity binding on an avidity ELISA. The quantitative ELISA results were compared with an immunofluorescence antibody (IFA) assay, also in development, showing similar results.

Seneca Valley virus (SVV) is a member of the family Picornaviridae, genus *Senecavirus*. *Senecavirus* A (SVA) is a recently identified single-stranded RNA virus closely related to members of the *Cardioviruses* genus. SVV was originally identified as a cell culture contaminant and was not associated with disease until 2007 when it was first observed in pigs with Idiopathic Vesicular Disease (IVD). Vesicular disease is sporadically observed in swine, is not debilitating, but is significant due to its resemblance to foreign animals diseases, such as foot and mouth disease. IVD disrupts swine production until foreign animal diseases can be ruled out. Identifying and characterizing SVA as a cause of IVD can help to quickly rule out infection by foreign animal diseases.

IVD has been observed recently in Canada, the United States, and Brazil, with vesicular foreign animal disease being ruled out while SVA was present. A quick test to diagnose SVA infection is necessary to help rule out infection by foreign animals disease. As of now, SVA infection is diagnosed by RT-PCR, a serum neutralizing assay, IFA, or cELISA (complement-enzyme-linked immunosorbent assay). RT-PCR is a quick and easy way to determine if animals are infected with or if vesicles contain SVA, but a negative result may mean that the animal has already cleared the infection; it cannot be properly interpreted as meaning that the animal was never infected. Detecting antibodies to SVA can determine whether an animal has been infected and is still protected against infection. Although serum neutralizing assays and IFA can measure the presence of serum antibodies, ELISAs are quicker and less expensive assays. A rapid, specific, and sensitive assay for detecting SVA-specific antibodies is needed. A cELISA for detecting SVA antibodies is available, but requires an antibody competition between well characterized monoclonal antibodies and serum antibodies for binding to viral antigen. An indirect ELISA only requires a purified antigen. An indirect ELISA is not yet available for the detection of anti-SVA antibodies in pigs.

This disclosure describes the development and characterization of an indirect ELISA assay to identify serum antibodies to SVA. Viral protein 1, 2 and 3 (VP1, VP2, VP3) were expressed, isolated, and purified from *E. coli* and used to coat plates for an indirect ELISA. This ELISA can now be used to help differentially diagnose IVD due to SVA helping to quickly rule out the presence of economically devastating foreign animal disease.

The SVA VP1, VP2, and VP3 proteins were cloned, expressed, and purified. Protein preparations were observed to be >90% pure (FIG. 1). ELISA plates were coated with 500 ng/well of VP1, VP2, or VP3 protein and samples were examined for anti-SVA antibody reactivity. As a negative control, samples from a farm that was clinically negative and PCR negative for SVA were analyzed. These samples were used to determine the cut-off values for negative ($<OD_{avg}+$ 1StdDev) and positive samples ($>OD_{avg}+$2StdDev). Suspect positive samples occurred if the OD value fell between the negative and positive sample cut-off values.

The SVA ELISA was tested using samples from a farm showing clinical signs. A time course of samples starting at the day clinical signs were first observed (Day 0) and sampled up to 60 days post-break (Days 4, 11, 18, 25, 39, 60) were examined. ELISAs using VP1, VP2, or VP3 protein were performed (FIG. 2). The VP2 protein gave the largest range of OD values and the biggest difference between positive and negative sample values. The VP2 protein was used for further ELISA analysis of samples for SVA.

An ELISA using a combination of 100 ng of each VP1, VP2, and VP3 proteins was also performed on negative samples as well as on the time course samples. Results correlated with that of VP2 alone ($r^2=0.927$, $p<0.0001$), although background values for the combination ELISA were higher (data not shown).

Examination of negative samples, positive samples, and backgrounds were used to optimize the ELISA. Coating of the ELISA plates with 200 ng/well of each protein was chosen for further analysis of samples. A ROC analysis was performed using 116 negative samples and 205 positive samples to determine optimal cut-off values for the VP2 ELISA. The area under the curve to differentiate positive from negative values was 0.9622 with a p value <0.0001. A positive sample cut-off value of OD>0.6 was selected to identify positive samples. This gives a sensitivity of 94.2% and a specificity of 89.7%.

An avidity ELISA was performed on a subset of negative samples as well as the samples over a time course of infection. The avidity index was determined at each time point for those samples that were tested as ELISA positive (OD>0.6 cut-off). Both the average avidity index and the number of samples with a high avidity index (AI>50%) increased over time (FIG. 3). This suggests that the avidity index may be able to be used as an indicator of the amount of time that has passed since original infection.

An SVA immunofluorescence assay (IFA) was developed at the University of Minnesota diagnostic lab and is in the process of being validated. A set of SVA negative samples as well as the time course samples were examined by IFA. A comparison between positive and negative IFA and ELISA results was performed at each time point. The percent of samples that matched (either both positive or both negative) at each time point or in the negative samples is shown in FIG. 5. By 4 days after clinical signs were first observed, the two assays correlated in 81% of samples. However, on the day that clinical signs were first observed, the two assays only correlated in 40% of samples, with many samples positive by ELISA, but negative or suspect by IFA. This suggests that ELISA is able to detect SVA antibodies earlier than the IFA test.

The incidence of SVA cases has greatly increased since the middle of 2015. Due to the similarity of SVA symptoms to the symptoms of foreign animal disease (FAD, such as FMDV), which present as vesicular disease, SVA causes a halt in animal movement and production until FAD is ruled out. Diagnostics that can quickly identify SVA as the cause of IVD, as well as running diagnostics to rule out FAD, are necessary for maintaining healthy and efficient swine production. The SVA VP2 ELISA described herein is sensitive and specific for the diagnosis of SVA-specific antibodies.

The SVA ELISA uses the SVA VP2 protein as the antigen to determine the presence of antibodies to SVA, thus suggesting past infection by SVA. The sensitivity (94.2%) and specificity (89.7%) of the ELISA are such that infected herds will be easily identified. SVA antibodies continue to be observed at 60 days post-clinical signs and should continue to be present longer than that. Analysis of the avidity of the antibodies has been shown to differentiate between antibodies from early in infection (up to 18 days post-clinical signs) to those from later time points (25 days or more after clinical signs first observed), thus allowing for an approximation of when the herd was infected.

A comparison of the ELISA results with that of an IFA test showed that ELISA was more sensitive in diagnosing early time points of infection. At later time points in infection ELISA and IFA were both able to identify SVA positive animals at similar rates.

This SVA VP2 ELISA can quickly and effectively detect SVA antibodies present in swine. Identification of SVA infection as the cause of IVD can help to quickly rule out the presence of economically devastating foreign animal diseases in swine and allow the farm to return to normal production after clinical signs have resolved.

This disclosure therefore describes, in one aspect, a device and a method for detecting SVA antibodies in a biological sample obtained from a subject. Generally, the device includes a *Senecavirus* A polypeptide immobilized to the substrate. The *Senecavirus* A polypeptide includes a portion of SEQ ID NO:1. In various embodiments, the *Senecavirus* A polypeptide includes the SVA VP2 (amino acids 151-434 of SEQ ID NO:1), SVA VP1 (amino acids 674-937 of SEQ ID NO:1), or SVA VP3 (amino acids 435-673 of SEQ ID NO:1). In one particular embodiment, the *Senecavirus* A polypeptide includes the SVA VP2 (amino acids 151-434 of SEQ ID NO:1). In other embodiments, however, the *Senecavirus* A polypeptide can include a fragment of VP1, VP2, or VP3. Exemplary fragment of VP2 that can form the basis of a *Senecavirus* A polypeptide include amino acids 162-167 of SEQ ID NO:1, amino acids 179-190 of SEQ ID NO:1, amino acids 223-241 of SEQ ID NO:1, amino acids 252-294 of SEQ ID NO:1, amino acids 325-333 of SEQ ID NO:1, amino acids 344-359 of SEQ ID NO:1, amino acids 364-373 of SEQ ID NO:1, amino acids 386-397 of SEQ ID NO:1, or amino acids 409-417 of SEQ ID NO:1.

In some embodiments, the *Senecavirus* A polypeptide can include one or more amino acids appended to the N-terminal or the C-terminal of the VP1, VP2, or VP3 amino acid sequence. Exemplary amino acids additions include, for example, the MYC-tag (EQKLISEEDL, SEQ ID NO:2) or the 6×His-tag (HHHHHH, SEQ ID NO:3) or both in combination. In the preferred embodiment, the MYC-tag is positioned at the N-terminus and the 6×His-tag is positioned at the C-terminus. Other embodiments include production of chimeric proteins containing the VP1, VP2, or VP3 amino acid sequence fused in frame at either the N-terminus or the C-terminus to various other proteins (or a fragment thereof) including, but not limited to, glutathione-S-transferase, maltose-binding protein, streptavidin, and the streptavidin-binding peptide. In still other embodiments, a *Senecavirus* A polypeptide can include additional amino acids from SEQ ID NO:1, so long as the *Senecavirus* A polypeptide contains no more than about 1000 amino acids of SEQ ID NO:1. Thus, in some embodiments, the *Senecavirus* A polypeptide can include up to approximately 800 amino acids.

In use, the device may be contacted with at least a portion of sample from a subject that has been, or is at risk of having been, exposed to *Senecavirus* A. The portion of the sample is contacted with the device under conditions effective to allow antibody in the sample to specifically bind to the *Senecavirus* A polypeptide. As used herein, the term "specifically bind" refers to having a differential or a non-general affinity, to any degree, for a particular target such as the *Senecavirus* A polypeptide. In some cases, the specificity of the binding can be established by allowing antibody to specifically bind to the *Senecavirus* A polypeptide, then washing away antibody (and other components of the sample) that do not bind to the *Senecavirus* A polypeptide or that exhibit only general, non-differential binding to the *Senecavirus* A polypeptide.

The antibody remaining after the wash forms a complex with the *Senecavirus* A polypeptide that may be detected by any suitable method. In one exemplary embodiment, the antibody-*Senecavirus* A polypeptide complex may be detected using a secondary antibody that binds to antibody produced by the subject from which the biological sample was obtained. In a second exemplary embodiment, the antibody-*Senecavirus* A polypeptide complex may be detected by reactivity with *Senecavirus* A polypeptide that is modified in the same way as a secondary antibody so that it can be detected. Another exemplary embodiment involves the use of a blocking assay, in which a labeled antibody (e.g., a monoclonal antibody) against the *Senecavirus* A polypeptide is applied to the device in combination with the sample. The presence of sample antibodies specific for *Senecavirus* A polypeptide is inferred from the reduction in reactivity of the labeled antibody due to competition with sample antibodies.

In another aspect, this disclosure describes a composition that includes any embodiment of the *Senecavirus* A polypeptide described immediately above and an adjuvant. The composition may be used to provide treatment of a subject having or at risk of having a *Senecavirus* A infection. As used herein, "treat," "treatment," and variations thereof refer to reducing, limiting progression, ameliorating, or resolving, to any extent, the symptoms or signs related to a condition. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. As used herein, "symptom" refers to any subjective evidence of disease or of a patient's condition, while "sign" or "clinical sign" refers to an objective physical finding relating to a particular condition capable of being found by one other than the patient. The term "at risk" refers to a subject that may or may not actually possess the described risk. Thus, for example, a subject "at risk" of infection by *Senecavirus* A (SVA) is a subject present in an area where individuals have been identified as infected by SVA and/or is likely to be exposed to SVA even if the subject has not yet manifested any detectable indication of infection by SVA and regardless of whether the subject may harbor a subclinical amount of SVA.

A composition that includes a *Senecavirus* A polypeptide may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the *Senecavirus* A polypeptide, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the *Senecavirus* A polypeptide without causing any undesirable biological effects or interacting in a deleterious manner with any of the other components of the pharmaceutical composition in which it is contained.

The *Senecavirus* A polypeptide may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, percutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, the composition may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the *Senecavirus* A polypeptide into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of *Senecavirus* A polypeptide administered can vary depending on various factors including, but not limited to, the specific *Senecavirus* A polypeptide included in the composition, the weight, physical condition, and/or age of the subject, and/or the route of administration. Thus, the absolute weight of *Senecavirus* A polypeptide included in a given unit dosage form can vary widely, and depends upon factors such as the species, age, weight and physical condition of the subject, and/or the method of administration. Accordingly, it is not practical to set forth generally the amount that constitutes an amount of *Senecavirus* A polypeptide effective for all possible applications. Those of ordinary skill in the art, however, can readily determine the appropriate amount with due consideration of such factors.

In some embodiments, the method can include administering sufficient *Senecavirus* A polypeptide to provide a dose of, for example, from about 20 µg to 200 µg to the subject, although in some embodiments the methods may be performed by administering *Senecavirus* A polypeptide in a dose outside this range. In some of these embodiments, the method includes administering sufficient *Senecavirus* A polypeptide to provide a dose of 20 µg to 100 µg per animal per dose.

In some embodiments, *Senecavirus* A polypeptide may be administered, for example, from a single dose to multiple doses at an interval of one week up to four weeks, although in some embodiments the method can be performed by administering *Senecavirus* A polypeptide at a frequency outside this range. In certain embodiments, *Senecavirus* A polypeptide may be administered once or twice or three times in the first four to eight weeks of life. *Senecavirus* A polypeptide might also be administered to naïve juveniles or adults not previously administered *Senecavirus* A polypeptide in the same manner, or to previously administered juveniles or adults in the same manner at intervals of time as a boost to maintain a positive immune status. The interval of time may vary from 3 months to 12 months.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Cloning, Expression and Purification of SVA VP1, VP2, and VP3 Protein

The full-length gene sequence for SVA VP1, VP2, and VP3 strain 11-55910-3 (Genbank ID AGM16001) was optimized for expression in *E. coli* and the optimized genes were synthesized (Integrated DNA Technologies, Inc., Coralville, Iowa) and cloned into a modified pET24b vector (Novagen, Madison, Wis.; Puvanendiran et al., *Virus Res* 157(1):92-98, 2011) using the In-Fusion cloning kit (Clontech, Mountain View, Calif.) following the manufacturer's directions. Gene sequences for VP1, VP2, and VP3 antigens were confirmed by sequencing. Protein expression and purification was performed as previously described (Dvorak et al., *Veterinary Microbiology* 189:86-90, 2016). Purity was analyzed by SDS-PAGE and concentration was determined using the Quick start Bradford protein assay following manufacturer's instructions (Bio-Rad laboratories, Inc., Hercules, Calif.) using a Bio-tek Epoch plate reader (BioTek Instruments, Inc., Winooski, Vt.).

Serum Samples

Porcine serum samples were obtained from the University of Minnesota Diagnostic laboratory. Samples included serum from presumed SVA negative farms and an SVA positive farm sampled over a 60-day time course following the observation of clinical signs (noted as day 0).

Antibody Detection by ELISA and IFA

Detection of antibodies to SVA VP1, VP2, and VP3 protein was performed by indirect ELISA as previously described (Puvanendiran et al., *Virus Res* 157(1):92-98, 2011; Dvorak et al., *Veterinary Microbiology* 189:86-90, 2016). Before optimization of the assay, the test samples were run on plates coated with 500 ng of antigen/well. Plates for the optimized VP2 ELISA were coated with 200 ng/well. Positive and negative serum samples were run on each plate.

An avidity ELISA was performed following the ELISA protocol above with the addition of a guanidine wash step. Before secondary antibody was added, 1 M guanidine in phosphate-buffered saline containing 0.05% Tween 20 (PBST), pH 7.4, was added to each well and incubated for 10 minutes. Plates were then washed as usual, secondary antibody was added, and the remainder of the protocol was performed as usual. The avidity index was determined by dividing the OD of the sample with guanidine by the OD of the sample without guanidine multiplied by 100: $(OD_{Gn+}/OD_{Gn-}) \times 100$.

Human lung cancer NCI-H1299 cells were inoculated with SVA strain isolated from a 2015 outbreak in the U.S.A. Infected cells were washed with PBS, fixed with acetone and incubated using two-fold dilutions of serum from 1:20 to 1:320 at 27° C. for one hour. Fluorescein-labeled goat anti-pig IgG was diluted 1:50 in PBS, added into the wells and incubated at 37° C. for one hour. The cells were observed under fluorescence microscopy. A positive signal at a sample dilution of 1:20 was considered suspect and 1:40 or higher was considered to be positive.

Statistical Methods

ELISA analysis and comparison to the IFA results were performed using GraphPad Prism software (Version 5.0a, GraphPad Software, Inc., La Jolla, Calif.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

```
Senecavirus A polyprotein (AGM16001.1)
                                                              SEQ ID NO: 1
  1    MQNSHFSFDT ASGTFEDVTG TKVKIVEYPR SVNNGVYDSS THLEILNLQG EIEILRSFNE

61    YQIRAAKQQL GLDIVYELQG NVQTTSKNDF DSRGNNGNMT FNYYANTYQN SVDFSTSSSA

121    SGAGPGNSRG GLAGLLTNFS GILNPLGYLK DHNTEEMENS ADRVITQTAG NTAINTQSSL

181    GVLCAYVEDP TKSDPPSSST DQPTTTFTAI DRWYTGRLNS WTKAVKTFSF QAVPLPGAFL

241    SRQGGLNGGA FTATLHRHFL MKCGWQVQVQ CNLTQFHQGA LLVAMVPETT LDVKPDGKAK

301    SLQELNEEQW VEMSDDYRTG KNMPFQSLGT YYRPPNWTWG PNFINPYQVT VFPHQILNAR

361    TSTSVDISVP YIGETPTQSS ETQNSWTLLV MVLVPLDYKE GATTDPEITF SVRPTSPYFN

421    GLRNRYTTGT DEEQGPIPTA PRENSLMFLS TIPDDTVPAY GNVRTPPVNY LPGEITDLLQ

481    LARIPTLMAF GRVSEPEPAS DAYVPYVAVP TQFDDKPLIS FPITLSDPVY QNTLVGAISS

541    NFANYRGCIQ ITLTFCGPMM ARGKFLLSYS PPNGTQPQTL SEAMQCTYSI WDIGLNSSWT

601    FVIPYISPSD YRETRAITNS VYSADGWFSL HKLTKITLPP DCPQKPCILF FASAGEDYTL

661    RLPVDCNPSY VFHSTDNAET GVIEAGNTDT DFSGELAAPG SNHTNVKFLF DRSRLLNVIK

721    VLEKDAVFPR PFPTETGAQQ DDGYFCLLTP RPTVASRPAT RFGLYVNPSD SGVLANTSLD

781    FNFYSLACFT YFRSDLEVTV VSLEPDLEFA VGWFPSGSEY QASSFVYDQL HVPYHFTGRT

841    PRAFTSKGGK VSFVLPWNSV SSVLPVRWGA ASKLSSATRG LPAHADWGTI YAFVPRPNEK
```

```
 901   KSTAVKHVAV YVRYKNARAW CPSMLPFRSY KQKMLMQSGD IETNPGPASD NPILEFLEAE

961   NDLVTLASLW KMVHSVQQTW RKYVKNDNFW PNLLSELVGE GSIALAATLS NQASVKALLG

1021   LHFLSRGLNY TDFYSLLIEK CSSFFTVEPP PPPAENLMTK PSVKSKFRKL FKMQGPMDKV

1081   KDWNQIAAGL KNFQFVRDLV KEVVDWLQAW INKEKASPVL QYQLEMKKLG PVALAHDAFM

1141   AGSGPPLSDD QIEYLQNLKS LALTLGKTNL AQSLTTMINA KQSSAQRVEP VVVVLRGKPG

1201   CGKSLASTLI AQAVSKRLYG SQSVYSLPPD PDFFDGYKGQ FVTLMDDLGQ NPDGQDFSTF

1261   CQMVSTAQFL PNMADLAEKG RPFTSNLIIA TTNLPHFSPV TIADPSAVSR RINYDLTLEV

1321   SEAYKKHTRL NFDLAFRRTD APPIYPFAAH VPFVDVAVRF KNGHQNFNLL ELVDSICADI

1381   RAKQQGARNM QTLVLQSPNE NDDTPVDEAL GRVLTPAAVD EALVDLAPEA DPVGRLAILA

1441   KLGLALAAVT PGLIILAVGL YRYFSGSDTD QDETECEEST KAPRSENAYD GPKKNSKPPG

1501   ALSLMEMQQP NVDMGFEAAV AKKVVVPITF MVPNRPSGLT QSALLVAGRT FLINEHTWSN

1561   PSWTSFTIRG EVHTRDEPFQ TVHFTHHGVP TDLMMVRLGP GNSFPNNLDK FGLDQMPARN

1621   SRVVGVSSSY GNFFFSGNFL GFVDSITSEQ GTYARLFRYR VTTYKGWCGS ALVCEAGGVR

1681   RIIGLHSAGA AGIGAGTYIS KLGLIKALKH LGEPLATMQG LMTELEPGIT VHVPRKSKLR

1741   KTTAHAVYKP EFEPAVLSKF DPRLNKDVDL DEVIWSKHTA NVPYQPPLFY TYMSEYAHRV

1801   FSFLGKDNDI LTVKEAILGI PGLDPMDPHT APGLPYAING LRRTDLVDFV NGTVDAALAM

1861   QIQKFLDGDY SDHVFQTFLK DEIRPSEKVR AGKTRIVDVP SLAHCIVGRM LLGRFAAKFQ

1921   SHPGFLLGSA IGSDPDVFWT VIGAQLEGRK NTYDVDYSAF DSSHGTGSFE ALISHFFTVD

1981   NGFSPALGPY LRSLAVSVHA YGERRIKITG GLPSGCAATS LLNTVLNNVI IRTALALTYK

2041   EFEYDMVDII AYGDDLLVGT DYDLDFNEVA RRAAKLGYKM TPANKGSVFP PTSSLSDAVF

2101   LKRKFVQNND GLYKPVMDLK NLEAMLSYFK PGTLLEKLQS VSMLAQHSGK EEYDRLMHPF

2161   ADYGAVPSHE YLQARWRALF D
```

---

What is claimed is:

1. A device comprising:
   a substrate; and
   a *Senecavirus* A polypeptide immobilized to the substrate, the *Senecavirus* A polypeptide comprising:
   a fragment of amino acids 151-434 of SEQ ID NO:1, the fragment comprising at least:
   amino acids 162-167 of SEQ ID NO:1,
   amino acids 179-190 of SEQ ID NO:1,
   amino acids 223-241 of SEQ ID NO:1, or
   amino acids 252-294 of SEQ ID NO:1; or
   at least a portion of amino acids 674-937 of SEQ ID NO:1.

2. The device of claim 1 wherein the fragment of amino acids 151-434 of SEQ ID NO:1 further comprises:
   amino acids 325-333 of SEQ ID NO:1,
   amino acids 344-359 of SEQ ID NO:1,
   amino acids 364-373 of SEQ ID NO:1,
   amino acids 386-397 of SEQ ID NO:1, or
   amino acids 409-417 of SEQ ID NO:1.

3. A method for detecting antibody that specifically binds to a *Senecavirus* A polypeptide in a biological sample obtained from a subject, the method comprising:
   contacting at least a portion of the sample with a *Senecavirus* A polypeptide, the *Senecavirus* A polypeptide comprising:
   a fragment of amino acids 151-434 of SEQ ID NO:1, the fragment comprising at least:
   amino acids 162-167 of SEQ ID NO:1,
   amino acids 179-190 of SEQ ID NO:1,
   amino acids 223-241 of SEQ ID NO:1, or
   amino acids 252-294 of SEQ ID NO:1; or
   at least a portion of amino acids 674-937 of SEQ ID NO:1; and
   detecting antibody from the biological sample specifically bound to the *Senecavirus* A polypeptide.

4. The method of claim 3 wherein the *Senecavirus* A polypeptide is immobilized to a substrate.

5. The method of claim 3, wherein the fragment of amino acids 151-434 of SEQ ID NO:1 further comprises:
   amino acids 325-333 of SEQ ID NO:1,
   amino acids 344-359 of SEQ ID NO:1,
   amino acids 364-373 of SEQ ID NO:1,
   amino acids 386-397 of SEQ ID NO:1, or
   amino acids 409-417 of SEQ ID NO:1.

6. A composition comprising:
   a *Senecavirus* A polypeptide comprising:
   a fragment of amino acids 151-434 of SEQ ID NO:1, the fragment comprising at least:
   amino acids 162-167 of SEQ ID NO:1,
   amino acids 179-190 of SEQ ID NO:1,
   amino acids 223-241 of SEQ ID NO:1, or
   amino acids 252-294 of SEQ ID NO:1; or
   at least a portion of amino acids 674-937 of SEQ ID NO:1; and
   an adjuvant.

7. The composition of claim 6, wherein the fragment of amino acids 151-434 of SEQ ID NO:1 further comprises:
   amino acids 325-333 of SEQ ID NO:1,
   amino acids 344-359 of SEQ ID NO:1,
   amino acids 364-373 of SEQ ID NO:1,
   amino acids 386-397 of SEQ ID NO:1, or
   amino acids 409-417 of SEQ ID NO:1.

* * * * *